United States Patent
Mattes et al.

(10) Patent No.: US 11,801,141 B2
(45) Date of Patent: Oct. 31, 2023

(54) MEDICAL PRODUCT, PREFERABLY FOR USE DURING THE TREATMENT OF A BONE CAVITY, METHOD FOR PRODUCING THE MEDICAL PRODUCT, AND MEDICAL KIT

(71) Applicant: Aesculap AG, Tuttlingen (DE)

(72) Inventors: Ursula Mattes, Renquishausen (DE); Michael Utz, Tuttlingen (DE)

(73) Assignee: AESCULAP AG, Tuttlingen (DE)

(*) Notice: Subject to any disclaimer, the term of this patent is extended or adjusted under 35 U.S.C. 154(b) by 317 days.

(21) Appl. No.: 16/311,625

(22) PCT Filed: Jun. 20, 2017

(86) PCT No.: PCT/EP2017/065144
§ 371 (c)(1),
(2) Date: Dec. 19, 2018

(87) PCT Pub. No.: WO2017/220617
PCT Pub. Date: Nov. 28, 2017

(65) Prior Publication Data
US 2019/0231530 A1    Aug. 1, 2019

(30) Foreign Application Priority Data

Jun. 22, 2016 (DE) ..................... 10 2016 211 201.5

(51) Int. Cl.
*A61F 2/28* (2006.01)
*A61L 27/58* (2006.01)
(Continued)

(52) U.S. Cl.
CPC ................ *A61F 2/28* (2013.01); *A61L 27/54* (2013.01); *A61L 27/58* (2013.01);
(Continued)

(58) Field of Classification Search
CPC .. A61F 2002/30032; A61F 2002/30062; A61F 2002/30143; A61F 2002/30224;
(Continued)

(56) References Cited

U.S. PATENT DOCUMENTS

| 5,084,051 A | 1/1992 | Tormala et al. |
| 5,139,424 A | 8/1992 | Yli-Urpo |

(Continued)

FOREIGN PATENT DOCUMENTS

| CA | 2905816 | 9/2014 |
| CN | 104524639 | 4/2015 |

(Continued)

OTHER PUBLICATIONS

International Search Report dated Dec. 4, 2017, of corresponding International Patent Application No. PCT/EP2017/065144.

(Continued)

*Primary Examiner* — William H Matthews
(74) *Attorney, Agent, or Firm* — Lewis Kohn & Walker LLP; David M. Kohn (57) ABSTRACT

A medical product, preferably for use in the treatment, more particularly in the filling up and/or closure, of a bone cavity, the product having structural elements connected to one another, the structural elements being dividable at least into two groups of structural elements, namely at least into a first group of structural elements and into a second group of structural elements, the structural elements of the first group having a lower hardness than the structural elements of the second group. Furthermore, a method for producing the medical product and a medical kit.

30 Claims, 3 Drawing Sheets

(51) Int. Cl.
*A61L 27/54* (2006.01)
*A61F 2/30* (2006.01)

(52) U.S. Cl.
CPC .............. *A61F 2002/2835* (2013.01); *A61F 2002/2839* (2013.01); *A61F 2002/30062* (2013.01); *A61F 2002/30069* (2013.01); *A61F 2002/30115* (2013.01); *A61F 2002/30143* (2013.01); *A61F 2002/30149* (2013.01); *A61F 2002/30156* (2013.01); *A61F 2002/30677* (2013.01); *A61F 2002/30985* (2013.01); *A61L 2430/02* (2013.01)

(58) Field of Classification Search
CPC .. A61F 2002/30242; A61F 2002/30303; A61F 2002/30971; A61F 2002/2835; A61F 2/2846; A61F 2/28; A61F 2002/285; A61F 2002/30004; A61F 2002/30014; A61F 2002/30016; A61F 2/02; A61L 27/56; A61L 2430/02
See application file for complete search history.

(56) References Cited

U.S. PATENT DOCUMENTS

| | | | |
|---|---|---|---|
| 5,730,743 | A | 3/1998 | Kirsch et al. |
| 7,905,921 | B2 * | 3/2011 | Kim ............. A61F 2/4611 623/17.16 |
| 9,408,697 | B2 | 8/2016 | Faccioli et al. |
| 2002/0173850 | A1 | 11/2002 | Brodke et al. |
| 2003/0009225 | A1 | 1/2003 | Khandkar et al. |
| 2003/0138473 | A1 | 7/2003 | Koblish et al. |
| 2005/0042288 | A1 | 2/2005 | Koblish et al. |
| 2005/0049706 | A1 | 3/2005 | Brodke et al. |
| 2006/0088601 | A1 | 4/2006 | Overby et al. |
| 2007/0093904 | A1 | 4/2007 | Biedermann et al. |
| 2007/0122447 | A1 | 5/2007 | Koblish et al. |
| 2010/0010513 | A1 | 1/2010 | Yun et al. |
| 2012/0253474 | A1 | 10/2012 | Klein et al. |
| 2014/0121776 | A1 * | 5/2014 | Hunt ............. A61F 2/2803 623/17.16 |
| 2014/0199657 | A1 | 7/2014 | Moon et al. |
| 2015/0039097 | A1 * | 2/2015 | Biris ............. A61L 27/46 623/23.51 |
| 2015/0289979 | A1 | 10/2015 | Gabelle et al. |
| 2017/0239054 | A1 | 8/2017 | Engstrand et al. |

FOREIGN PATENT DOCUMENTS

| | | |
|---|---|---|
| CN | 104623728 | 5/2015 |
| DE | 102012213246 | 1/2014 |
| WO | 9856301 | 12/1998 |

OTHER PUBLICATIONS

Chinese Office Action dated Dec. 15, 2020, of corresponding Chinese Patent Application No. 201780051688.8.
Chinese Office Action dated Jul. 27, 2020, of corresponding Chinese Patent Application No. 201780051688.8.
Chinese Office Action dated May 11, 2021, of corresponding Chinese Patent Application No. 201780051688.8.
Japanese Office Action dated Apr. 14, 2021, of corresponding Japanese Patent Application No. 2018-567152.

* cited by examiner

MEDICAL PRODUCT, PREFERABLY FOR USE DURING THE TREATMENT OF A BONE CAVITY, METHOD FOR PRODUCING THE MEDICAL PRODUCT, AND MEDICAL KIT

FIELD OF APPLICATION AND PRIOR ART

The invention relates to a medical product and a medical kit which are both suitable in particular for use in the treatment of a bone cavity, and to a method for producing such a medical product.

Especially in the case of revision operations after a total hip or knee arthroplasty, there is frequently the need to fill up cavitary bone defects. Filling up bone defects is in some cases also necessary in the area of spine and trauma surgery.

Especially in the case of osteoporotic and tumor-afflicted bones, it is, however, frequently difficult to fill up cavitary bone defects.

Multiple treatment options are available today for filling up bone cavities intraoperatively.

One treatment option consists in the use of patient-endogenous bone. Alternatively, it is possible to use bones from a bone bank. If both options are not available, use must be made of either a metallic bone substitute material or a cementitious bone substitute material, such as, for example, calcium phosphate, hydroxyapatite or the like. Said materials are generally present either as a hard, pressed shaped part or as a loose powder. The adaptation of these solid, artificial bone substitute materials is, intraoperatively, very difficult to impossible, meaning that it is frequently not possible to completely fill up bone cavities and that voids remain in the cavities.

A further disadvantage is that, in many cases, generic bone substitute materials can be implanted into bone cavities having small access openings only in an inadequate manner. Pulverulent bone substitute materials can be introduced more effectively into such cavities. However, pulverulent bone substitute materials have the disadvantage that they only have load-bearing properties to a limited extent.

OBJECT AND ACHIEVEMENT

It is therefore an object of the present invention to provide a medical product and also a method for producing a medical product, wherein the product is to be suitable especially for the treatment of bone cavities and is to avoid, as far as possible, particularly disadvantages of bone substitute implants and bone substitute materials that are known from the prior art.

It is further an object of the invention to provide a medical kit usable especially for the treatment of bone cavities.

These objects are achieved by a medical product for use in the filling up and/or closure of a bone cavity having structural elements connected to one another, characterized in that the structural elements are dividable into at least two groups of structural elements, namely at least into a first group of structural elements and into a second group of structural elements, the structural elements of the first group having a lower hardness than the structural elements of the second group, a method characterized in that the product is produced by means of a 3D-printing process, and a medical kit for use in the filling up and/or closure of a bone cavity, comprising a medical product as claimed and an attachment means, such as preferably a suture material or at least one bone screw. Preferred embodiments are defined in the dependent claims. The object of the invention is further achieved by a treatment method disclosed in the description.

The wording of all the claims is hereby incorporated in the present description by express reference.

According to a first aspect, the invention relates to a medical product, preferably for use in the treatment, more particularly for use in the filling up and/or in the closure, of a bone cavity.

The medical product has structural elements connected to one another. The structural elements are dividable into at least two groups of structural elements, namely at least into a first group of structural elements and into a second group of structural elements.

The medical product is distinguished by the structural elements of the first group having a lower hardness than the structural elements of the second group. In other words, the medical product is distinguished by having structural elements with different hardnesses, namely at least one first group of structural elements and one second group of structural elements, the structural elements of the first group having a lower hardness than the structural elements of the second group.

Different hardnesses of the structural elements bring about, in particular, differences in the strengths, more particularly tensile, compressive and/or bending strengths, of the structural elements. This allows, with particular advantage, a better, more particularly more variable, matching of the medical product with specific features such as, in particular, dimensions/shape and access opening of a bone cavity. At the same time, mechanical properties of the medical product that are necessary for a lasting treatment of a bone cavity can be influenced or controlled in a specific manner via the design of the structural elements, more particularly via the selection of materials for their production.

The products produced have, in particular, the advantage that they have the tendency, owing to the flexible structural elements present, to spread out in a bone cavity. As a result, the bone cavity fills up. In this process, the individual structural elements line up against one another and thus form a stable, load-bearing construct. In this connection, the load-bearing properties of the construct stem mainly from the structural elements of the second group. Through appropriate positioning of the products, it is also possible to close the opening of a bone cavity, since the product can be placed over the opening from the inside of the cavity.

In the context of the present invention, the expression "hardness" is to be understood to mean the mechanical resistance which is put up by a material to the mechanical penetration of another body (penetration body) (so-called penetration hardness). The hardness is generally calculated by the quotient of test force (F) and indentation area (A).

The hardness of plastics or polymers, more particularly elastomers, can, for example, be determined in accordance with the standards DIN EN ISO 868 and DIN ISO 7619-1. Here, a spring-loaded hardened-steel pin of a Shore hardness tester is pushed into a material to be tested. The depth of penetration of the pin into the material to be tested is a measure of the Shore hardness, which is measured on a scale of from 0 Shore (2.5 mm penetration depth) to 100 Shore (0 mm penetration depth). A high number thus means a great hardness. In the case of the Shore hardness tester, it is possible to use an additional device which presses the sample to be measured onto the measurement table with a force of 12.5 N in the case of Shore A or 50 N in the case of Shore D. The nominal temperature for the measurement of Shore hardness is generally 23° C. and is preferably restricted to the temperature interval of +/−2 K.

Shore A is reported especially in the case of soft elastomers. The penetration body used is a needle with a blunt tip. The end face of the truncated cone has a diameter of 0.79 mm, and the opening angle is 35°. The resting weight is 1 kg and the holding time is 15 s.

Shore D is reported especially in the case of tough elastomers after measurement with a needle which ends with a 30° angle and has a spherical tip with a diameter of 0.2 mm. The resting weight is 5 kg and the holding time is likewise 15 s.

The hardness of homogeneous, thin-walled or surface-hardened materials can, for example, be determined by means of Vickers hardness testing (VHN). Here, an equilateral diamond pyramid with an opening angle of 136° is pushed into the workpiece under a defined test force. The indentation area is calculated from the length of the diagonals of the remaining indentation, as determined by means of a measurement microscope. The ratio of test force (in N) to the indentation area d (in mm) yields, multiplied by the factor of 0.1891, the Vickers hardness number (VHN). The test force F can be 0.098 N≤F<1.961 N (Vickers microhardness testing), 1.961 N≤F<49.03 N (Vickers small-force hardness testing) or F≥49.03 N (Vickers hardness testing).

The hardness of metals can, for example, be measured by means of instrumented penetration testing in accordance with DIN EN ISO 14577. Here, a penetration body of specific geometry, for example a pyramid-shaped penetration body (Vickers pyramid), is pushed into a material to be tested. Test force and penetration depth are measured simultaneously. The harder the material, the lower the penetration depth of the penetration body.

In agreement with the preceding embodiments, the structural elements of the first group put up a smaller mechanical resistance to the penetration of a penetration body (such as, for example, a pin, a needle or a pyramid) than the structural elements of the second group to the penetration of the same penetration body in the present invention. The penetration of a penetration body into a structural element of the first group therefore leads to a greater penetration depth than the penetration of the same penetration body into a structural element of the second group.

In the context of the present invention, the expression "bone cavity" is to be understood to mean a void in a human or animal bone, more particularly human or animal joint bone, preferably human or animal hip-joint or knee-joint bone, or human or animal vertebral body. The void can be the result of a bone fracture, a bone trauma, a bone disease, a tumor disease or a surgical intervention/reintervention, more particularly a revision operation after a total hip or knee arthroplasty.

In a particularly preferred embodiment, the medical product is an implant, preferably a bone substitute material or bone filler material.

Preferably, the structural elements of the first group primarily provide for a desired matchability of the medical product with bone cavities. It is therefore preferred when the structural elements of the first group are flexible or bendy, more particularly elastic. In the context of the present invention, the structural elements of the first group can therefore also be referred to as flexible structural elements. Particularly preferably, the structural elements of the first group are more flexible or more bendy, more particularly more elastic, than the structural elements of the second group. As a result, it is possible to achieve a particularly effective matching of the medical product with a bone cavity, more particularly with an access opening thereof.

In contrast, the structural elements of the second group are preferably primarily responsible for the mechanical stability, such as dimensional stability, of the medical product. It is therefore preferred when the structural elements of the second group are load-bearing or dimensionally stable. In the context of the present invention, the structural elements of the second group can therefore also be referred to as load-bearing or dimensionally stable structural elements. Particularly preferably, the structural elements of the second group are more load-bearing or more dimensionally stable than the structural elements of the first group. As a result, it is possible, with particular advantage, to ensure that the medical product has sufficient mechanical stability in order to be able to treat, more particularly fill up and/or close, a bone cavity in a long-term manner.

In a further embodiment, the medical product is deformable to a limited extent. In said embodiment, a deformability of the medical product is preferably attributed to the structural elements of the first group, whereas the structural elements of the second group preferably limit a deformability of the product.

In a further embodiment, the medical product is reversibly deformable. In said embodiment, elastic structural elements of the first group are preferably responsible for a reversible deformability of the medical product, whereas the structural elements of the second group preferably limit a reversible deformability of the product.

In a further embodiment, the structural elements of the first group have in each case a hardness (Shore D) of from 30 to 100, more particularly from 35 to 80, preferably from 40 to 60.

If the structural elements of the second group comprise a metal or consist of a metal, the structural elements of the second group have, in a further embodiment, in each case a Vickers hardness number of from 100 to 1700, more particularly from 150 to 800, preferably from 200 to 600, at a test force of 10 N.

If the structural elements of the second group comprise a surface-hardened plastic, more particularly a surface-hardened plastic with a coating, or consist of such a plastic, the structural elements of the second group have, in a further embodiment, in each case a Vickers hardness number of from 100 to 1700, more particularly from 150 to 800, preferably from 200 to 600, at a test load or test mass of 0.025 g.

In a further embodiment, the structural elements of the first group have a lower strength, more particularly a lower tensile strength, a lower compressive strength or a lower bending strength, such as lower bending tensile strength, than the structural elements of the second group.

The structural elements of the first group can have, in particular, a tensile strength of from 1 $N/mm^2$ to 30 $N/mm^2$, more particularly from 5 $N/mm^2$ to 28 $N/mm^2$, preferably from 7 $N/mm^2$ to 25 $N/mm^2$.

The structural elements of the second group can have, in particular, a tensile strength of from 50 $N/mm^2$ to 1100 $N/mm^2$, more particularly from 60 $N/mm^2$ to 900 $N/mm^2$, preferably from 70 $N/mm^2$ to 900 $N/mm^2$.

Furthermore, the structural elements of the first group can have, in particular, a compressive strength of from 5 $N/mm^2$ to 150 $N/mm^2$, more particularly from 10 $N/mm^2$ to 100 $N/mm^2$, preferably from 12 $N/mm^2$ to 90 $N/mm^2$.

Furthermore, the structural elements of the second group can have, in particular, a compressive strength of from 100 $N/mm^2$ to 3000 $N/mm^2$, more particularly from 150 $N/mm^2$ to 2000 $N/mm^2$, preferably from 150 $N/mm^2$ to 1500 $N/mm^2$.

Furthermore, the structural elements of the first group can have, in particular, a bending strength, such as bending tensile strength, of from 3 N/mm$^2$ to 100 N/mm$^2$, more particularly from 5 N/mm$^2$ to 80 N/mm$^2$, preferably from 10 N/mm$^2$ to 50 N/mm$^2$.

Furthermore, the structural elements of the second group can have, in particular, a bending strength, such as bending tensile strength, of from 30 N/mm$^2$ to 630 N/mm$^2$, more particularly from 40 N/mm$^2$ to 500 N/mm$^2$, preferably from 50 N/mm$^2$ to 400 N/mm$^2$.

In a further embodiment, the structural elements of the first group are identical.

In a further embodiment, the structural elements of the first group are dividable into two or more subgroups, the structural elements of each subgroup being identical to one another and the structural elements of different subgroups being different from one another. For example, the structural elements of different subgroups can be different from one another with regard to their hardness, strength (such as tensile, compressive and/or bending strength), their shape or form, their dimensions (such as, for example, length, breadth, thickness or height, radius and/or diameter) and/or their material.

In a further embodiment, the structural elements of the second group are identical.

In a further embodiment, the structural elements of the second group are dividable into two or more subgroups, the structural elements of each subgroup being identical to one another and the structural elements of different subgroups being different from one another. For example, the structural elements of different subgroups can be different from one another with regard to their hardness, strength (such as tensile, compressive and/or bending strength), their shape or form, their dimensions (such as, for example, length, breadth, thickness or height, radius and/or diameter) and/or their material.

In a further embodiment, the structural elements of the first group are in each case elongated structural elements, i.e., structural elements having a length-to-width ratio or length-to-diameter ratio >(spoken as "greater than") 1. What is possible as a result is, with particular advantage, an at least sectional surrounding (bordering) or edging of the structural elements of the second group by the structural elements of the first group. The structural elements of the first group can, in particular, be bar-shaped. In a further embodiment, the structural elements of the first group have a thickness-to-width ratio (height-to-width ratio)>(spoken as "greater than") or <(spoken as "less than") 1. Owing to such ratios, the flexibility and/or stability of the medical product can be influenced in a specific manner and, in particular, matched with a bone cavity to be treated.

In a further embodiment, the structural elements of the first group have a cross section variable across the structural element length. In this connection, the cross section can vary with respect to its dimensions and/or its outline along the structural element length. For example, the structural elements of the first group can be in the shape of a truncated cone.

In a further embodiment, the structural elements of the second group are in each case in the form of cylinders, more particularly flat cylinders, having circular or polygonal end faces. The polygonal end faces can, in particular, be triangle-shaped, quadrangle-shaped, such as square- or rectangle-shaped, pentagon-shaped, hexagon-shaped or be combinations of two different end faces of the ones mentioned.

In principle, the structural elements of the first group and the structural elements of the second group can have in each case the same width or the same diameter.

Alternatively, the structural elements of the first group can have in each case a smaller width or a smaller diameter than the structural elements of the second group or vice versa, i.e., the structural elements of the second group can have in each case a smaller width or a smaller diameter than the structural elements of the first group.

In a further embodiment, the structural elements of the first group have in each case a lower mass than the structural elements of the second group. As a result, it is possible to achieve an additional improvement in the matchability of the medical product with a bone cavity.

In principle, the structural elements of the first group and/or the structural elements of the second group can have a number of holes, i.e., one hole or multiple holes. The hole(s) can be in the form of (an) indentation(s) and/or of (an) opening(s), i.e., in the form of (a) breach(es).

According to the invention, it may be preferred when only the structural elements of the first group have a number of holes. Alternatively, the structural elements of the first group can have a larger number of holes and/or larger holes than the structural elements of the second group. This can contribute, with particular advantage, to an increase in the flexibility, more particularly bendability, of the structural elements of the first group compared to the structural elements of the second group, the result being that the matchability of the medical product with a bone cavity can be additionally improved.

In a further embodiment, the medical product has a planar structure constructed from the structural elements of the first and second groups. Preferably, the length and the width of the planar structure are each larger than the thickness or height of the planar structure. The planar structure is preferably a sheet- or carpet-shaped planar structure.

In a further embodiment, the medical product, more particularly the planar structure, has a varying, i.e., nonconstant, thickness or height. For example, the medical product, more particularly the planar structure, can have a varying thickness of from 0.1 mm to 10 mm, more particularly from 0.3 mm to 5 mm, preferably from 0.5 mm to 1.5 mm.

In an alternative embodiment, the medical product, more particularly the planar structure, has a constant, i.e., steady or uniform, thickness. For example, the medical product, more particularly the planar structure, can have a constant thickness of from 0.1 mm to 10 mm, more particularly from 0.3 mm to 5 mm, preferably from 0.5 mm to 1.5 mm.

In one embodiment which is advantageous from an attachment point of view, edge regions, more particularly corner regions, of the medical product, more particularly of the planar structure, have a number of attachers, i.e., one attacher or multiple attachers, or a number of holes, i.e., one hole or multiple holes, for an attacher. The holes can, for example, be breaches or openings of structural elements, more particularly of structural elements of the first group. Such structural elements can, in particular, be formed at the edge regions, more particularly corner regions, of the medical product, more particularly of the planar structure. The breaches or openings allow, for example, the threading of surgical suture materials or the engagement of bone screws, the result being that a secure attachment of the medical product, more particularly of the planar structure, in a bone cavity is possible. Therefore, the attachers can, for example, be surgical suture materials or bone screws.

In a further embodiment, the medical product, more particularly the planar structure, has a thickening which is formed at least sectionally along the edge of the medical product, more particularly of the planar structure. Therefore, the thickening can be a kind of edge web. Preferably, the thickening is a circumferential thickening, i.e., a thickening which is continuous along the edge of the medical product, more particularly of the planar structure. According to the invention, it is further preferred when the thickening is formed by structural elements of the first group. The thickening can, for example, be based on a broader configuration of the structural elements of the first group compared with the structural elements of the second group. The thickening described in this paragraph has, in particular, the advantage that it can be connected to attachers, as described for example in the preceding paragraph, or provided with holes for the accommodation or for the engagement of attachers. In addition, the thickening can achieve a higher stability of the outer edge of the medical product, more particularly of the planar structure.

In a further embodiment, structural elements of the first group that are connected to one another form a number of intended bending regions, i.e., one intended bending region or a plurality of intended bending regions, for example two, three, four, five, six, seven, eight, nine, ten, eleven, twelve or more intended bending regions, of the medical product, more particularly of the planar structure.

The plural expression "intended bending regions" used hereinafter can, in line with the remark made in the preceding paragraph in relation to the expression "number of intended bending regions", mean one intended bending region (singular) or a plurality of intended bending regions (plural). Preferably, the plural expression "intended bending regions" used hereinafter means, however, a plurality of intended bending regions.

Preferably, the intended bending regions surround in each case at least one, more particularly just one, structural element of the second group. In other words, it is preferred according to the invention when the intended bending regions form in each case a surround for at least one, more particularly just one, structural element of the second group.

The intended bending regions can surround the at least one structural element of the second group especially in a cornerless manner, for example in the shape of a circular ring.

Alternatively, the intended bending regions can surround the at least one structural element of the second group in a polygonal manner, more particularly in the shape of a triangle, in the shape of a quadrangle, such as in the shape of a square or rectangle, in the shape of a pentagon and/or in the shape of a hexagon, preferably in the shape of a triangle, in the shape of a quadrangle, such as in the shape of a square or rectangle, in the shape of a pentagon or in the shape of a hexagon.

Furthermore, the intended bending regions preferably run in rows or in a linear manner, more particularly in a straight manner.

Furthermore, the intended bending regions cannot run in a straight manner, more particularly in a zigzag manner, in a curved manner, in an arched manner or in a meandering manner, such as in a sinusoidal manner.

In a further embodiment, the intended bending regions run in a longitudinal direction, in a width direction and/or in a slant direction, more particularly diagonal direction, of the medical product, more particularly of the planar structure.

Furthermore, the intended bending regions can run in parallel to one another.

In particular, the intended bending regions can be in the form of rows arranged in parallel to one another.

Alternatively, the intended bending regions can be arranged relative to one another in an angle, more particularly orthogonally, i.e., in a right angle.

The intended bending regions are preferably folding regions of the medical product, more particularly of the planar structure.

In a further embodiment, the intended bending regions are connected to one another at least in part via a structural element of the second group or via multiple structural elements of the second group.

In a further embodiment, the structural elements of the first group comprise a resorbable material or consist of a resorbable material. In a further embodiment, the structural elements of the second group comprise a resorbable material or consist of a resorbable material. More particularly, the structural elements of the first group and the structural elements of the second group can comprise a resorbable material or consist of a resorbable material. However, according to the invention, it may be preferred when only the structural elements of the first group comprise a resorbable material or consist of a resorbable material. The use of a resorbable material for the structural elements of the first group and/or for the structural elements of the second group can, in particular, be advantageous for the formation of a medical product having osteoconductive properties, since a resorption process within a bone cavity can have a beneficial effect on the ingrowth of bone tissue into the cavity.

The resorbable material can, in particular, be selected from the group consisting of polymer, such as polyhydroxyalkanoate, elastomer, protein, such as extracellular protein, polysaccharide, such as cellulose derivative and/or mucopolysaccharide, bone cement material, metal and combinations, more particularly composites, mixtures or blends, of at least two of the stated materials.

The polymer, more particularly polyhydroxyalkanoate, can, in particular, be selected from the group consisting of polylactic acid or polylactide, polyglycolic acid or polyglycolide, poly-3-hydroxybutyrate, poly-4-hydroxybutyrate, polytrimethylene carbonate, poly-ε-caprolactone, stereoisomers, more particularly diastereomers, thereof, copolymers thereof and combinations, more particularly composites, mixtures or blends, of at least two of the stated polymers.

The protein can be selected from the group consisting of collagen, gelatin, elastin, reticulin, fibronectin, laminin, fibrin, fibrinogen, albumin, such as serum albumin, salts thereof, stereoisomers, more particularly diastereomers, thereof and combinations, more particularly composites, mixtures or blends, of at least two of the stated proteins.

The polysaccharide can, in particular, be selected from the group consisting of starch, amylose, amylopectin, dextran, dextrin, cellulose, alkylcellulose, hydroxyalkylcellulose, hydroxy methylcellulose, hydroxyethylcellulose, hydroxypropylcellulose, carboxyalkylcellulose, carboxymethylcellulose, chitin, chitosan, hyaluronic acid, dextran sulfate, heparin, heparan sulfate, chondroitin sulfate, dermatan sulfate, salts thereof, stereoisomers, more particularly diastereomers, thereof and combinations, more particularly composites, mixtures or blends, of at least two of the stated polysaccharides.

The bone cement material can, in particular, comprise a calcium and/or magnesium compound or consist of a calcium and/or magnesium compound which is selected from the group consisting of monocalcium phosphate monohydrate (MCPM), monocalcium phosphate anhydride (MCPA), dicalcium phosphate, dicalcium phosphate anhydride (DCPA), dicalcium phosphate dihydrate (DCPD), octacalcium phosphate (OCP), tricalcium phosphate, α-tricalcium phosphate (α-TCP), β-tricalcium phosphate (β-TCP), amorphous calcium phosphate (ACP), hydroxyapatite (HA), calcium-deficient hydroxyapatite (CdHA), substituted hydroxyapatite, nonstoichiometric hydroxyapatite, nanoscale hydroxyapatite, tetracalcium phosphate (TTCP), calcium sulfate ($CaSO_4$), calcium sulfate hemihydrate ($CaSO_4 \times 0.5H_2O$), calcium sulfate dihydrate ($CaSO_4 \times 2H_2O$), calcium oxide (CaO), calcium hydroxide ($Ca(OH)_2$), calcium carbonate ($CaCO_3$), calcium glycerophosphate, calcium citrate, calcium lactate, calcium acetate, calcium tartrate, calcium chloride ($CaCl_2$)), calcium silicates, magnesium hydrogen phosphate ($MgHPO_4$) in the form of the hydrates or as anhydrous substance, trimagnesium phosphate ($Mg_3(PO_4)_2$), magnesium dihydrogen phosphate ($Mg(H_2PO_4)_2$) in the form of the hydrates or as anhydrous substance, magnesium chloride ($MgCl_2$) in the form of the hydrates or as anhydrous substance, magnesium glycerophosphate, magnesium hydroxide ($Mg(OH)_2$), magnesium hydroxide carbonate (e.g., as $4MgCO_3 \times Mg(OH)_2 \times 5H_2O$), magnesium oxide (MgO), magnesium citrates ($Mg_3(C_6H_5O_7)_2$ or $Mg(C_6H_6O_7)$), calcium magnesium carbonate ($CaMg(CO_3)_2$, dolomite and mixtures of at least two of the stated compounds.

The metal can, in particular, be selected from the group consisting of magnesium, tantalum and combinations, more particularly alloys, thereof.

In a further embodiment, the structural elements of the first group comprise a nonresorbable material or consist of a nonresorbable material. In a further embodiment, the structural elements of the second group comprise a nonresorbable material or consist of a nonresorbable material. More particularly, the structural elements of the first group and the structural elements of the second group can comprise a nonresorbable material or consist of a nonresorbable material. However, according to the invention, it may be preferred when only the structural elements of the second group comprise a nonresorbable material or consist of a nonresorbable material. Owing to the use of a nonresorbable material for the structural elements of the first group and/or for the structural elements of the second group, it is possible, in particular, to form a long-term product having mechanical properties which remain constant in a (substantially) long-term manner.

The nonresorbable material can, in particular, be selected from the group consisting of polymer or plastic, elastomer, thermoplastic, plastic, polyolefin, polyester, polyamide, polyether, polycarbonate, silicones, surface-hardened plastic, ceramic, metal and combinations, more particularly composites, mixtures or blends, of at least two of the stated materials.

The polyolefin can, in particular, be selected from the group consisting of polyethylene, low-density polyethylene, high-density polyethylene, ultrahigh-molecular-weight polyethylene (UHMWPE), polypropylene, polytetrafluoroethylene, polyvinylidene chloride, polyvinylidene fluoride, polytetrafluoropropylene, polyhexafluoropropylene, polyacrylate, polymethyl acrylate, polymethyl methacrylate, copolymers thereof and combinations, more particularly composites, mixtures or blends, of at least two of the stated polyolefins.

The polyester can, in particular, be selected from the group consisting of polyethylene terephthalate, polypropylene terephthalate, polybutylene terephthalate, copolymers thereof and combinations, more particularly composites, mixtures or blends, of at least two of the stated polyesters.

The polyamide can, in particular, be selected from the group consisting of nylon 6 (polyamide made from caprolactam), nylon 46 (polyamide made from tetramethylenediamine and adipic acid), nylon 6,6 (polyamide made from hexamethylenediamine and adipic acid), nylon 69 (polyamide made from hexamethylenediamine and azelaic acid), nylon 6,12 (polyamide made from hexamethylenediamine and dodecanedioic acid), nylon 1010 (polyamide made from 1,10-decanediamine and sebacic acid), nylon 11 (polyamide made from α-aminoundecanoic acid), nylon 12 (polyamide made from laurolactam), nylon 1212 (polyamide made from dodecanediamine and dodecanedioic acid), silk, copolymers thereof and combinations, more particularly composites, mixtures or blends, of at least two of the stated polyamides.

The polyether can, in particular, be selected from the group consisting of polyetherketone (PEK), polyetheretherketone (PEEK), polyetherketoneketone (PEKK), polyoxymethylene (POM) and combinations, more particularly composites, mixtures or blends, of at least two of the stated polyethers.

The elastomer can be selected from the group consisting of thermoplastic elastomer, more particularly olefin-based or urethane-based thermoplastic elastomer, thermoplastic polyurethane, thermoplastic copolyamide, thermoplastic polyester elastomer, thermoplastic copolyester, styrene block copolymer and combinations, more particularly composites, mixtures or blends, of at least two of the stated elastomers.

The ceramic can, in particular, be selected from the group consisting of aluminum oxide ceramic, delta ceramic, forte ceramic and combinations, more particularly composites, of at least two of the stated ceramics.

The metal can, in particular, be selected from the group consisting of titanium, zirconium, vanadium, chromium, molybdenum, iron, cobalt, nickel, palladium, platinum, copper, silver, gold and combinations, more particularly alloys, thereof. A suitable alloy is, for example, a cobalt-chromium-molybdenum alloy.

In a further embodiment, the structural elements of the first group comprise a different material or consist of a different material compared to the structural elements of the second group. With regard to suitable materials, reference is made to the materials described in the preceding paragraphs.

For example, the structural elements of the first group can comprise a different resorbable material or consist of a different resorbable material compared to the structural elements of the second group. With regard to suitable materials, reference is made to the materials described in the preceding paragraphs.

Alternatively, the structural elements of the first group can comprise a different nonresorbable material or consist of a different nonresorbable material compared to the structural elements of the second group. With regard to suitable materials, reference is made to the materials described in the preceding paragraphs.

Preferably, the structural elements of the first group comprise a resorbable material or consist of a resorbable material, whereas the structural elements of the second group preferably comprise a nonresorbable material or consist of a nonresorbable material. As a result, it is possible, with particular advantage, to induce a neogenesis of bone tissue through the structural elements of the first group, whereas the structural elements of the second group can make a long-term contribution to the mechanical stability of a treated bone cavity.

Alternatively, the structural elements of the first group can comprise a nonresorbable material or consist of a nonresorbable material, whereas the structural elements of the second group can comprise a resorbable material or consist of a resorbable material.

In a further embodiment, the structural elements of the first group comprise an additive, more particularly a medical active ingredient, a biological active ingredient or a combination of said active ingredients. In a further embodiment, the structural elements of the second group comprise an additive, more particularly a medical active ingredient, a biological active ingredient or a combination of said active ingredients. In a further embodiment, the structural elements of the first group and the structural elements of the second group comprise an additive, more particularly a medical active ingredient, a biological active ingredient or a combination of said active ingredients.

The active ingredient is preferably selected from the group consisting of antimicrobial, more particularly antibiotic, active ingredient, wound healing-promoting active ingredient, disinfectant active ingredient, inflammation-inhibiting or anti-inflammatory active ingredient, blood coagulation-promoting active ingredient, growth factor, such as bone growth factor (osteoinductive factor), cell-differentiation factor, cell-adhesion factor, cell-recruitment factor, cell receptor, cell-binding factor, cytokine, peptide, structural protein, extracellular protein, such as collagen, elastin, reticulin and the like, serum protein, such as albumin, polysaccharide, such as hyaluronic acid, oligonucleotide, polynucleotide, DNA, RNA, salts thereof, stereoisomers, more particularly diastereomers, thereof and mixtures of at least two of the stated active ingredients.

Preferably, the active ingredient is a bone growth factor, more particularly a bone morphogenetic protein (BMP). The bone morphogenetic protein is preferably selected from the group consisting of bone morphogenetic protein 1 (BMP1), bone morphogenetic protein 2 (BMP2), bone morphogenetic protein 3 (BMP3), bone morphogenetic protein 3B (BMP3B), bone morphogenetic protein 4 (BMP4), bone morphogenetic protein 5 (BMP5), bone morphogenetic protein 6 (BMP6), bone morphogenetic protein 7 (BMP7), bone morphogenetic protein 8A (BMP8A), bone morphogenetic protein 8B (BMP8B), bone morphogenetic protein 10 (BMP10), bone morphogenetic protein 15 (BMP15) and mixtures of at least two of the stated bone morphogenetic proteins.

In a further embodiment, the structural elements of the first group have a coating containing an additive, more particularly a medical active ingredient, a biological active ingredient or a combination of said active ingredients. In a further embodiment, the structural elements of the second group have a coating containing an additive, more particularly a medical active ingredient, a biological active ingredient or a combination of said active ingredients. In a further embodiment, the structural elements of the first group and the structural elements of the second group have a coating containing an additive, more particularly a medical active ingredient, a biological active ingredient or a combination of said active ingredients. With regard to possible additives, more particularly active ingredients, reference is made to the additives, more particularly active ingredients, stated in the preceding paragraphs.

In a further embodiment, the structural elements of the first group have a different shape compared to the structural elements of the second group. In an alternative embodiment, the structural elements of the first group and the structural elements of the second group have in each case the same shape. With regard to suitable shapes, reference is made to the shapes stated in the following paragraph.

For example, the structural elements of the first group and/or the structural elements of the second group can in each case be present in the shape of a sphere, a cube, a cuboid, a prism, a parallelepiped, a ring, a toroid or a star. As already mentioned, what can also be envisaged according to the invention is that the structural elements of the first group and/or the structural elements of the second group differ from one another with respect to their shape. For example, the first group can have ring-shaped and cube-shaped structural elements, whereas the second group can, for example, have cuboid-shaped and cube-shaped structural elements.

In a further embodiment, the medical product is a medical product for use in the treatment, more particularly for use in the filling up and/or in the closure, of a
  bone cavity caused by trauma,
  bone cavity caused by disease, more particularly caused by tumor, or
  of a bone cavity caused by a surgical intervention or reintervention, more particularly of a bone cavity caused by a revision operation after a total hip or knee arthroplasty.

The bone cavity is preferably a joint bone cavity, long bone cavity or vertebral body cavity. Particularly preferably, the bone cavity is a hip joint bone cavity, knee-joint bone cavity, femoral cavity, tibial cavity, fibular cavity, humeral cavity, radial cavity or ulnar cavity.

In a further embodiment, the medical product, more particularly the planar structure, is present in the form of a continuous tape.

In a further embodiment, the medical product, more particularly the planar structure, is present in off-the-shelf form, more particularly in cut-to-length form.

According to a second aspect, the invention relates to a method for producing a medical product, preferably for use in the treatment, more particularly for use in the filling up and/or in the closure, of a bone cavity. Preferably, the product is a medical product according to a first aspect of the invention.

The method is particularly distinguished by the product being produced by means of a 3D-printing process or by means of additive manufacturing.

The present invention is furthermore based on the surprising discovery that it is possible by means of 3D-printing processes to produce medical products, especially in the form of a flexible sheet or in the manner of a "carpet", which are preferably usable for the treatment, more particularly for filling up and/or for closure, of a bone cavity.

In this connection, 3D-printing processes offer, in particular, the possibility of producing structural elements having different hardnesses, strengths (such as tensile strengths, compressive strengths and/or bending tensile strengths), different materials, different shapes or geometries, different dimensions (such as length, width and/or thickness) and the like and of connecting them to one another to form continuous and preferably flexible products. This means that 3D-printing processes allow, in particular, a tailor-made production of medical products for the treatment of bone cavities, the result being that, for example, a wide variety of different bone cavity dimensions and geometries and also, in particular, a wide variety of different mechanical stability requirements can be adequately taken into account.

In the context of the present invention, the expression "3D-printing processes" or "additive manufacturing" is to be understood to mean processes for the rapid and cost-effective manufacturing of models, samples, prototypes, tools and end products such as, in particular, medical products. These processes are frequently also referred to as "rapid prototyping". The manufacturing is done directly on the basis of internal computer data models from, in particular, shapeless material, for example from liquids, melts, powders or the like, or shape-neutral material, for example from tape- or wire-shaped material, by means of chemical and/or physical processes.

The 3D-printing process can be selected from the group consisting of powder-bed process, open-space process and liquid-material process.

The powder-bed process can be selected from the group consisting of selective laser melting, selective laser sintering, selective heat sintering, binder jetting and electron-beam melting.

The open-space process can be selected from the group consisting of fused deposition modeling, laminated object modeling process, cladding, wax deposition modeling, contour grafting, cold spray and electron-beam melting.

The liquid-material process can be selected from the group consisting of stereolithography, digital light processing process and LCM process. The LCM process can be a liquid composite molding process or a lithography-based ceramic manufacturing process.

With regard to further features and advantages of the method, more particularly of the medical product, reference is made in full to the remarks made in the context of the first aspect of the invention in order to avoid repetition.

According to a third aspect, the invention relates to a medical kit, preferably for use in the treatment, more particularly for use in the filling up and/or in the closure, of a bone cavity.

The medical kit is particularly distinguished by comprising a medical product according to a first aspect of the invention and also an attachment means.

Preferably, the medical product and the attachment means are spatially or physically separate from one another.

The attachment means can, for example, be a suture material.

Alternatively, the attachment means can be a bone screw or multiple bone screws.

Furthermore, the medical kit can comprise a further bone substitute material. The further bone substitute material can be an autologous bone substitute material. Furthermore, the further bone substitute material can be pulverulent. The use of a further bone substitute material has the advantage that it can be introduced into a bone cavity to be treated and then the bone cavity can be closed by means of the medical product according to the invention.

With regard to further features and advantages of the kit, more particularly of the medical product, reference is made in full to the remarks made in the context of the first and second aspect of the invention in order to avoid repetition.

According to a fourth aspect, the invention relates to a method for treating, more particularly filling up and/or closing, a bone cavity.

The method comprises the following step:
  introducing a medical product according to a first aspect of the invention into the bone cavity.

In a preferred embodiment, the method further comprises the following step:
  matching the medical product with a bone cavity, more particularly with the size of a bone cavity. The matching of the medical product is preferably performed before its introduction into the bone cavity.

In a further embodiment, the method further comprises the following step:
  attaching the medical product in the bone cavity. Preferably, the attachment is performed by means of an attachment means, such as, for example, a bone screw or a suture material.

With regard to further features and advantages of the method, more particularly of the medical product, reference is made in full to the remarks made in the context of the previous aspects of the invention in order to avoid repetition.

Further advantages and features of the invention are revealed by the claims and by the following description of preferred embodiments on the basis of examples and the associated figure descriptions. In this connection, features of the invention can, in each case, be realized on their own or in combination with one another. The embodiments described below serve to further elucidate the invention without restricting it thereto.

BRIEF DESCRIPTIONS OF THE FIGURES

In the figures, the following is shown schematically.

DETAILED DESCRIPTION OF THE FIGURES

Figure 1:
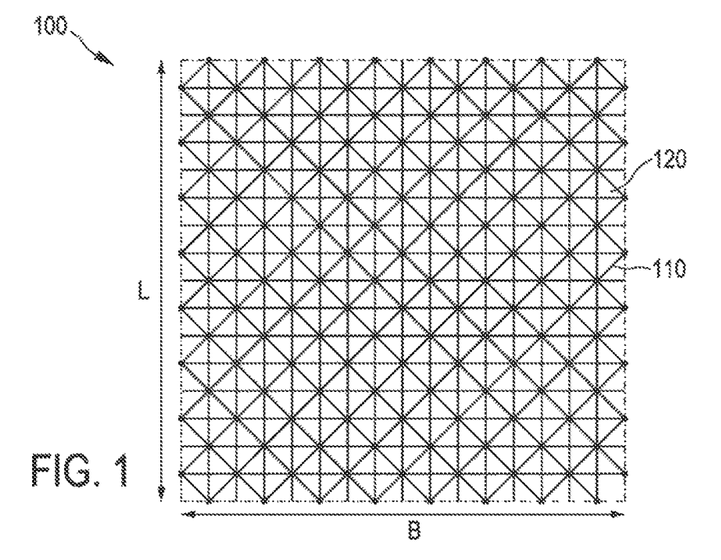
FIG. 1: shows one embodiment of a product according to the invention.

FIG. 1 shows schematically one embodiment of a medical product 100 according to the present invention.

The medical product 100 is preferably a bone substitute material or bone filler material.

The product 100 comprises a first group of structural elements 110 and a second group of structural elements 120. In this connection, the structural elements 110 have a lower hardness than the structural elements 120.

The different hardnesses of the structural elements 110 and 120 cause, in particular, different strengths of the structural elements 110 and 120. Preferably, the structural elements 110 are more elastic than the structural elements 120 and the structural elements 120 are more dimensionally stable than the structural elements 110.

The product 100 is present in the form of a planar structure. Preferably, the length L and the width B of the planar structure are each greater than the thickness of the planar structure. The planar structure can, in particular, be a sheet-shaped or carpet-type planar structure.

The structural elements 110 are in each case elongated, preferably bar-shaped, and surround in each case a structural element 120. In this connection, the structural elements 110 connected to one another form intended bending regions, more particularly folding regions, of the product 100, along which the product 100 can be bent, more particularly folded. As a result, the product 100 can, with particular advantage, be matched with different bone-cavity openings and shapes. The intended bending regions, more particularly folding regions, can, as depicted in FIG. 1, be formed in a longitudinal direction, in a width direction (or transverse direction) and in a diagonal direction of the product 100.

The structural elements 120 have in each case the shape of a cylinder, more particularly flat cylinder, having triangular end faces.

The structural elements 110 can, for example, be formed from a resorbable material such as polylactide, poly-4-hydroxybutyrate or collagen, or from a nonresorbable material, such as, for example, an aliphatic polyurethane, for example from a polyurethane commercially available under the name Vasomer. The structural elements 120 can, for example, be formed from a nonresorbable material such as ultrahigh-molecular-weight polyethylene (UHMWPE), polymethyl methacrylate, nylon 6,6 or polyetherketone.

Figure 2:
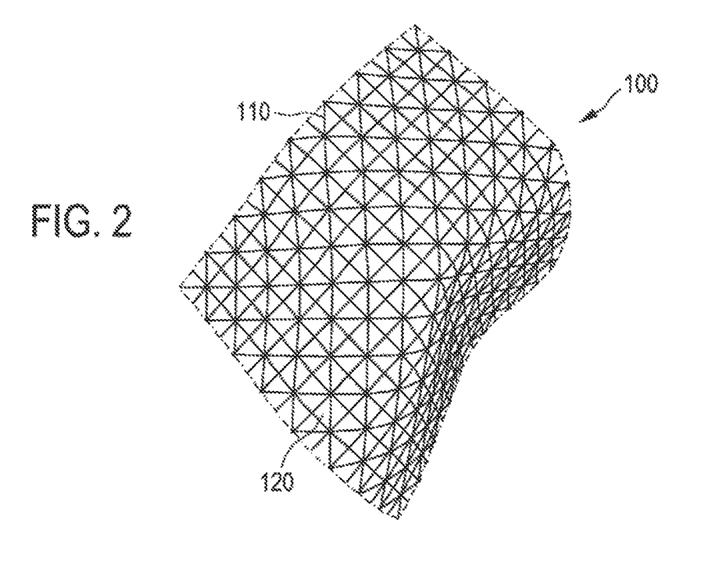
FIG. 2: shows a compressed, more particularly folded, state of the product depicted in FIG. 1,
FIG. 3: shows a more strongly compressed, more particularly folded, state of the product depicted in FIG. 1,
FIG. 4: shows a structural element of the first group.

A bending, more particularly folding, of the medical product 100 along intended bending regions, more particularly folding regions, formed by the structural elements 110 is indicated in FIG. 2.

Figure 3:
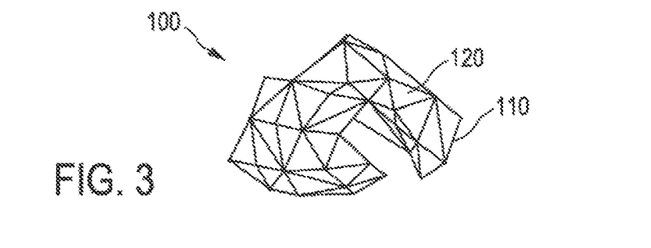

FIG. 3 shows schematically the product 100, as depicted in FIGS. 1 and 2, in a more strongly folded state. The product 100 can be transferred into such a state by bending, more particularly folding, along multiple intended bending regions, more particularly folding regions, formed by the structural elements.

Figure 4:
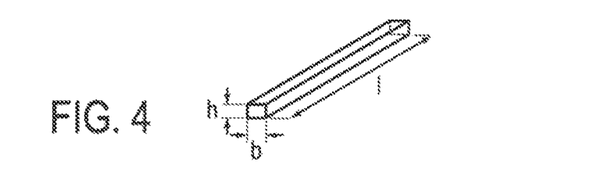

FIG. 4 shows schematically a structural element 110 of the medical product 100 depicted in FIGS. 1 to 3. The structural element 110 is elongated, preferably bar-shaped. For example, the structural element 110 can be in the form of a web having a quadrangular, more particularly rectangular, cross section. The structural element 110 has a length l, a width b and a thickness or height h.

Figure 5:
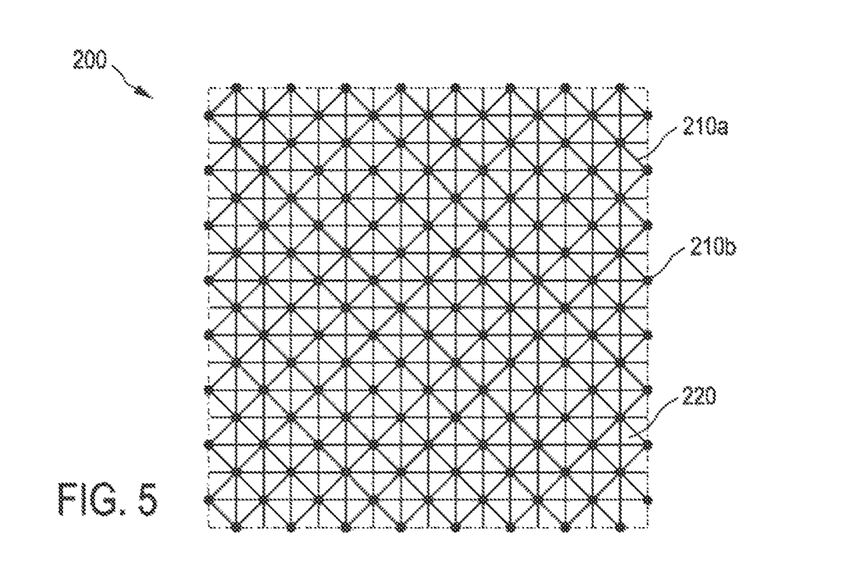
FIG. 5: shows a further embodiment of a product according to the invention

FIG. 5 shows schematically a further embodiment of an inventive product 200 according to the present invention.

The medical product 200 is likewise preferably a bone substitute material or bone filler material.

Compared with the medical product 100 depicted in FIGS. 1 to 3, the product 200 depicted in FIG. 5 differs in that the structural elements of the first group can be divided into two subgroups, namely into a first subgroup of structural elements 210a and into a second subgroup of structural elements 210b. In this connection, the structural elements 210a and 210b differ in particular with respect to their shape. Whereas the structural elements 210a are in each case elongated, more particularly bar-shaped, the structural elements 210b are in each case configured in the shape of a cylinder, more particularly flat cylinder, having circular end faces. Alternatively, the structural elements 210b can in each case be configured in the shape of a cylinder, more particularly flat cylinder, having polygonal, such as, for example, triangular, end faces (not depicted).

The structural elements 220 of the second group are in each case surrounded by three structural elements 210a and two structural elements 210b.

With regard to further features and advantages of the medical product 200 depicted in FIG. 5, reference is made to the preceding figure descriptions. The remarks made there with regard to the product 100 also apply mutatis mutandis to the product 200.

Figure 6:
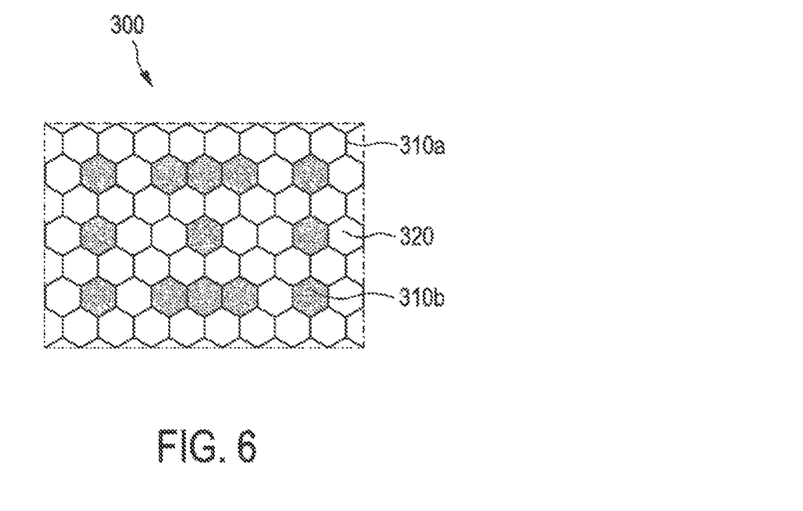
FIG. 6: shows a further embodiment of a product according to the invention.

FIG. 6 shows schematically a further embodiment of an inventive product 300.

In the case of the product 300, the structural elements of the first group can be divided into two subgroups, namely into a first subgroup of structural elements 310a and into a second subgroup of structural elements 310b. In this connection, the structural elements 310a and 310b differ in particular with respect to their shape. Whereas the structural elements 310a are in each case elongated, more particularly bar-shaped, the structural elements 310b are in each case configured in the shape of a cylinder, more particularly flat cylinder, having hexagonal end faces.

The structural elements 320 likewise have in each case the shape of a cylinder, more particularly flat cylinder, having hexagonal end faces.

The structural elements 320 are surrounded by the structural elements 310a and/or the structural elements 310b.

With regard to further features and advantages of the medical product 300 depicted in FIG. 6, reference is made to the remarks made in connection with FIGS. 1 to 4. The remarks made there with regard to the product 100 also apply mutatis mutandis to the product 300.

It is evident that the structural elements depicted in FIGS. 1 to 6 can also be formed from other materials. In this respect, reference is made in full to the materials stated in the general description.

The invention claimed is:

1. A medical product for use in the filling up and/or closure of a bone cavity having structural elements connected to one another, wherein the structural elements are dividable into at least two groups of structural elements, namely a first group of structural elements and a second group of structural elements, the structural elements of the first group having a lower hardness and a lower bending strength than the structural elements of the second group, wherein the structural elements of the first group that are connected to one another form a number of intended bending regions of the product and surround the structural elements of the second group, further wherein the structural elements of the first group are bar-shaped and these bar-shaped structural elements include holes or openings that extend through the body of the bar-shaped structural element, and wherein the structural elements of the second group are cylindrically shaped and do not include holes or openings, further wherein the intended bending regions formed from the structural elements of the first group are folding regions where the medical product is capable of being folded in more than one direction.

2. The medical product of claim 1 the product is an implant or a bone substitute material.

3. The medical product of claim 1, wherein the structural elements of the first group are flexible or bendy.

4. The medical product of claim 1, wherein the structural elements of the second group are dimensionally stable or load-bearing.

5. The medical product of claim 1, wherein the structural elements of the first group are identical or dividable into two or more subgroups, the structural elements of each subgroup being identical to one another and the structural elements of different subgroups being different from one another.

6. The medical product of claim 1, wherein the structural elements of the first group are elongated structural elements having a length-to-width ratio or length-to-diameter ratio greater than 1.

7. The medical product of claim 1, wherein the product has a planar structure constructed from the structural elements of the first and second group, the length and width of which planar structure is in each case larger than the thickness or height of said planar structure.

8. The medical product of claim 1, wherein the intended bending regions surround the at least one structural element of the second group in a cornerless manner.

9. The medical product of claim 1, wherein the intended bending regions surround the at least one structural element of the second group in a polygonal manner.

10. The medical product of claim 1, wherein the intended bending regions are in each case in rows.

11. The medical product of claim 1, wherein the intended bending regions are curved, arched, meandering or sinusoidal.

12. The medical product of claim 1, wherein the intended bending regions are connected to one another at least in part via one or more structural elements of the second group.

13. The medical product of claim 1, wherein the structural elements of the first and/or second group comprise a resorbable material or the structural elements of the first and/or second group consist of a resorbable material.

14. The medical product of claim 1, wherein the structural elements of the first and/or second group comprise a nonresorbable material or the structural elements of the first and/or second group consist of a nonresorbable material.

15. The medical product of claim 1, wherein the structural elements of the first and/or second group or a coating of the structural elements of the first and/or second group contain an additive.

16. A method for producing a medical product of claim 1, wherein the product is produced by means of a 3D-printing process.

17. A medical kit for use in the filling up and/or closure of a bone cavity, comprising: a medical product as claimed in claim 1; and an attachment means selected from the group consisting of a suture material and at least one bone screw.

18. The medical product of claim 1, wherein the structural elements of the first group are elastic.

19. The medical product of claim 7, wherein the planar structure is a sheet shaped planar structure.

20. The medical product of claim 1, wherein structural elements of the first group that are connected to one another form a number of intended bending regions of the planar structure.

21. The medical product of claim 1, wherein the intended bending regions surround in each case just one structural element of the second group.

22. The medical product of claim 1, wherein the intended bending regions surround the at least one structural element of the second group in the shape of a circular ring.

23. The medical product of claim 1, wherein the intended bending regions surround the at least one structural element of the second group in the shape of a triangle, in the shape of a quadrangle, in the shape of a pentagon and/or in the shape of a hexagon.

24. The medical product of claim 1, wherein the intended bending regions are in the form of rows arranged in parallel to one another.

25. The medical product of claim 13, wherein the material is selected from the group consisting of polyhydroxyalkanoate, protein, extracellular protein, polysaccharide, cellulose derivative, mucopolysaccharide, stereoisomers thereof, diastereomers thereof, salts thereof, copolymers thereof and combinations of at least two of the stated materials.

26. The medical product of claim 14, wherein the material is selected from the group consisting of polymer, polyolefin, polyester, polyamide, metal, ceramic and combinations of at least two of the stated materials.

27. The medical product of claim 15, wherein the additive is a medical and/or biological active ingredient.

28. The medical product of claim 27, wherein the medical and/or biological active ingredient is selected from the group consisting of antimicrobial active ingredient, antibiotic active ingredient, wound healing-promoting active ingredient, disinfectant active ingredient, inflammation-inhibiting or anti-inflammatory active ingredient, blood coagulation-promoting active ingredient, growth factor, bone growth factor (osteoinductive factor), cell-differentiation factor, cell-adhesion factor, cell-recruitment factor, cell receptor, cell-binding factor, cytokine, peptide, structural protein, extracellular protein, collagen, elastin, reticulin, serum protein, albumin, polysaccharide, hyaluronic acid, oligonucleotide, polynucleotide, DNA, RNA, salts thereof, stereoisomers thereof, diastereomers thereof and mixtures of at least two of the stated active ingredients.

29. A medical product for use in the filling up and/or closure of a bone cavity having structural elements connected to one another, wherein the structural elements are dividable into at least two groups of structural elements, namely a first group of structural elements and a second group of structural elements, the structural elements of the first group having a lower hardness and a lower bending strength than the structural elements of the second group, wherein the structural elements of the first group that are connected to one another form a number of intended bending regions of the product and surround the structural elements of the second group, and the structural elements of the first group are dividable into at least two subgroups comprising a first subgroup and a second subgroup, the structural elements of each subgroup being different from one another, further wherein the structural elements of the first subgroup are bar-shaped, the structural elements of the second subgroup are cylindrical with circular or polygonal end faces, and these bar-shaped structural elements of the first subgroup include holes or openings that extend through the body of the bar-shaped structural element, and wherein the structural elements of the second group are cylindrical and do not include holes or openings, further wherein the intended bending regions formed from the structural elements of the first group are folding regions where the medical product is capable of being folded in more than one direction.

30. A medical product for use in the filling up and/or closure of a bone cavity having structural elements connected to one another, wherein the structural elements are dividable into at least two groups of structural elements, namely a first group of structural elements and a second group of structural elements, the structural elements of the first group having a lower hardness and a lower bending strength than the structural elements of the second group, wherein the structural elements of the first group that are connected to one another form a number of intended bending regions of the medical product and surround the structural elements of the second group, further wherein the bending regions formed from the structural elements of the first group are folding regions allowing the medical product to fold in a longitudinal, transverse or diagonal direction, further wherein the structural elements of the first group are bar-shaped and these bar-shaped structural elements include holes or openings that extend through the body of the bar-shaped structural element, and wherein the structural elements of the second group are cylindrical and do not include holes or openings.

* * * * *